(12) United States Patent
Polley et al.

(10) Patent No.: US 8,764,441 B2
(45) Date of Patent: Jul. 1, 2014

(54) METHOD AND INTERNAL APPARATUS FOR DETERMINING FINAL POSITION OF DENTATE SKELETON IN ORTHOGNATHIC SURGERY

(76) Inventors: John W. Polley, River Forest, IL (US); Alvaro A. Figueroa, Glencoe, IL (US)

(*) Notice: Subject to any disclaimer, the term of this patent is extended or adjusted under 35 U.S.C. 154(b) by 488 days.

(21) Appl. No.: 12/840,814

(22) Filed: Jul. 21, 2010

(65) Prior Publication Data

US 2012/0022604 A1 Jan. 26, 2012

(51) Int. Cl.
*A61C 19/04* (2006.01)
*A61F 2/46* (2006.01)
*A61F 5/00* (2006.01)

(52) U.S. Cl.
USPC .............................. 433/73; 606/86 R; 606/87

(58) Field of Classification Search
USPC .............. 433/68–69, 72–76, 18–19; 606/280, 606/283–285, 286–297, 86 R, 87, 84, 90, 606/105, 71; 623/17.17–17.19
See application file for complete search history.

(56) References Cited

U.S. PATENT DOCUMENTS

| | | | | |
|---|---|---|---|---|
| 4,059,899 A | * | 11/1977 | Dyal | 433/72 |
| 4,189,835 A | | 2/1980 | Seldin | |
| 4,292,026 A | | 9/1981 | Yokota | |
| 4,573,917 A | | 3/1986 | Erickson | |
| 4,639,220 A | | 1/1987 | Nara et al. | |
| 5,409,017 A | * | 4/1995 | Lowe | 128/848 |
| 5,724,746 A | * | 3/1998 | Mack | 33/514 |
| 6,671,539 B2 | | 12/2003 | Gateno et al. | |
| 6,685,469 B2 | | 2/2004 | Chishti et al. | |
| 6,726,479 B2 | | 4/2004 | Tremont | |
| 6,827,574 B2 | * | 12/2004 | Payton | 433/8 |
| 6,971,877 B2 | * | 12/2005 | Harter | 433/75 |
| 7,377,778 B2 | | 5/2008 | Chishti et al. | |
| 8,282,635 B1 | * | 10/2012 | Amato | 606/57 |
| 2002/0156485 A1 | * | 10/2002 | Sellers et al. | 606/105 |
| 2003/0065259 A1 | | 4/2003 | Gateno et al. | |
| 2004/0166469 A1 | | 8/2004 | Tremont | |
| 2004/0219477 A1 | * | 11/2004 | Harter | 433/75 |
| 2009/0220122 A1 | | 9/2009 | Richards et al. | |
| 2010/0075270 A1 | * | 3/2010 | Figueroa et al. | 433/18 |
| 2010/0143855 A1 | | 6/2010 | Scheffler | |
| 2012/0277749 A1 | * | 11/2012 | Mootien et al. | 606/70 |

OTHER PUBLICATIONS

Xia, J.J., Gateno, J., Teichgraeber, J.F.: New clinical protocol to evaluate craniomaxillofacial deformity and plan surgical correction. J Oral Maxillofac Surg 67:2093-2106, 2009.

(Continued)

*Primary Examiner* — Yogesh Patel
(74) *Attorney, Agent, or Firm* — Fraser Clemens Martin & Miller LLC; William J. Clemens

(57) ABSTRACT

A skeletal positioning method and apparatus includes a splint having a main body coupled to a skeletal structure of a patient and a positioning guide having a skeletal footplate, a splint footplate, and an arm coupling the skeletal footplate and the splint footplate, the skeletal footplate including at least one aperture formed therein and the splint footplate including connectors for releasably coupling the positioning guide to the splint, wherein a relative position and orientation of the skeletal footplate and the splint footplate is pre-determined to align a portion of the skeletal footplate with a pre-defined portion of the skeletal structure of the patient.

19 Claims, 10 Drawing Sheets

(56) References Cited

OTHER PUBLICATIONS

Gateno, J., Xia J.J., Teichgraeber, J.F., et.al: Clinical feasibility of computer-aided surgical simulation (CASS) in the treatment of complex craniomaxillofacial deformities. J Oral Maxillofac Surg 65:728, 2007.

Mischkowski, R.A., Zinser, M.J., Ritter, L., et. al: Intra-operative navigation in the maxillofacial area based on 3-D imaging obtained by a cone-beam device. Int J Oral Maxillofac Surg 36:687, 2007.

Troulis, J.J., Everett, P., Setdin, E.B., et. al.: Development of a three-dimensional treatment planning system based on computed tomographic data. Int J Oral Maxillofac Surg 31:349, 2002.

Santler, G.: 3-D cosmos: A new 3-D model based computerized operation simulation and navigation system. J Maxillofac Surg 28:287, 2000.

Xia, J., Ip, H.H., Samman, N., et. al: Computer-assisted three-dimensional surgical planning and simulation: 3-D virtual osteotomy. Int J Oral Maxillofac Surg 29:11, 2000.

Xia, J., Samman, N., Yeung, R.W., et. al: Three-dimensional virtual reality surgical planning and simulation workbench for orthognathic surgery. Int J Adult Orthodon Orthognath Surg 15:265, 2000.

Xia, J., Samman, N., Yeung, R.W., et. al.: Computer-assisted three-dimensional surgical planning and simulation. 3-D soft tissue planning and prediction. Int J Oral Maxillofac Surg 29:250, 2000.

Stefanova, N., et. al.: "The Predictability of inferior Medial Canthus as a Stable External Vertical Reference Point in Maxillary Repositioning Surgery". Int J Adult Orthodon Orthognath Surg 15:305-308, 2000.

Manna, L., et. al.: "Technique for Vertical Positioning of the Maxilla After LeFort Osteotomy". J Oral Maxillofac Surg 54:652, 1996.

Perkins, S., et. al.: "A Modified Boley Gauge for Accurate Measurement During Maxillary Osteotomies". J Oral Maxillofac Surg 50:1018-1019, 1992.

Waldemar, D., Polido, et. al.: "An Assessment of the Predictability of Maxillary Surgery". J Oral Maxillofac Surg 48:697-701, 1990.

Heggie, A.A.C.: "A Calibrator for Monitoring Maxillary Incisor Position During Orthognathic Surgery". Oral Surg 64:671-673, 1987.

Van Sickels, J., et. al.: "Predictability of Maxillary Surgery: A Comparison of Internal and External Reference Marks." Oral Surg., 61:542-545, 1986.

Johnson, D.G. et. al.: "Intra-operative Measurement of Maxillary Repositioning: An Ancillary Technique." Oral Surg 60:266-268, 1985.

Erickson, K., et al., "Analytical Model Surgery", Modern Practice in Orthognathic Reconstructive Surgery, 1992, pp. 155 and 177-179, WB Saunders, US.

Bell, W., et al., "Art and Science of the Le Fort I Downfracture", The International Journal of Adult Orthodontics and Orthognathic Surgery, Jan. 1988, pp. 23-52, US.

Zinser, M., "Computer-Assisted Orthognatic Surgery Based on 3D Cephalometry: A New Approach With 3D Surgical Wavers", Journal of Oral and Maxillofacial Surgery, Sep. 2007, pp. 42, vol. 65, Issue 9, Supplement 1, Elsevier Inc., US.

\* cited by examiner

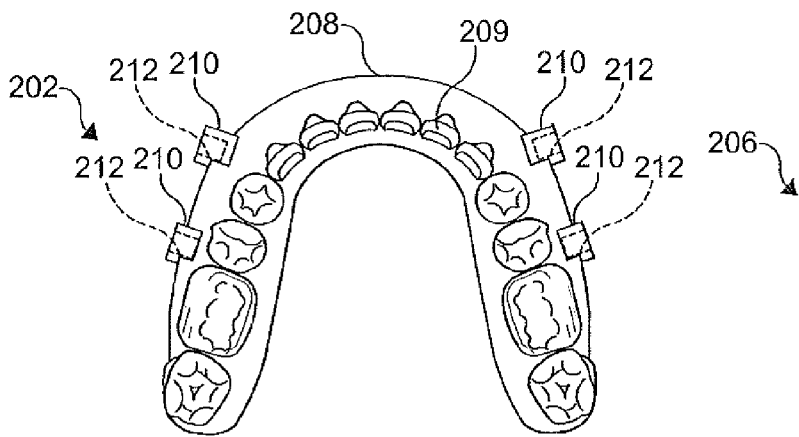
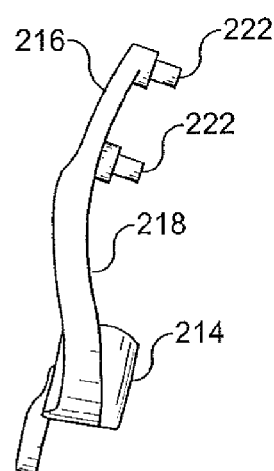
FIG. 16   FIG. 17
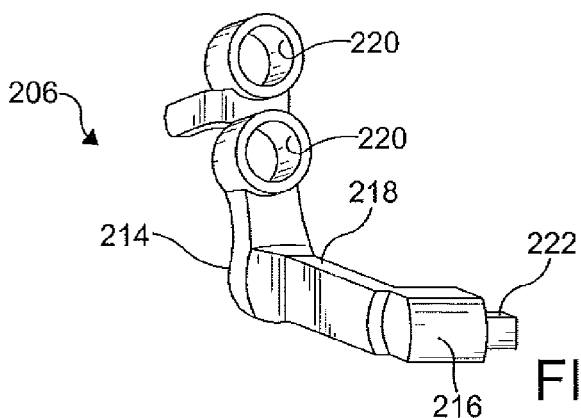
FIG. 18
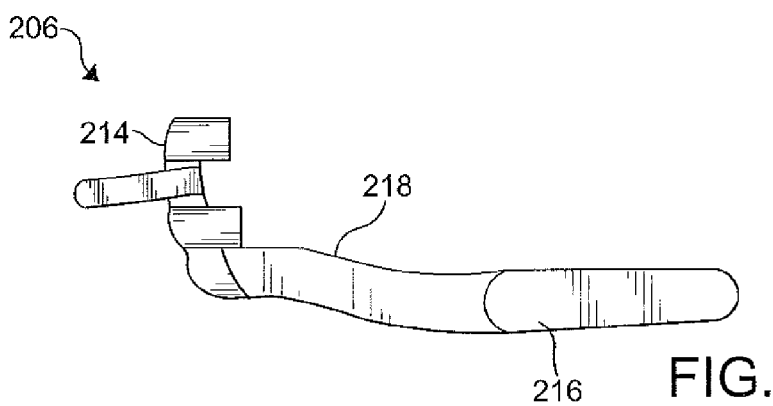
FIG. 19

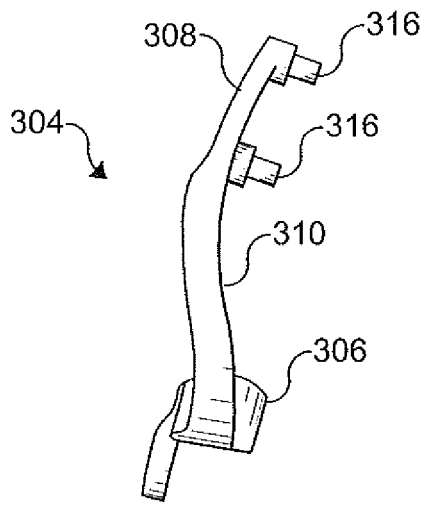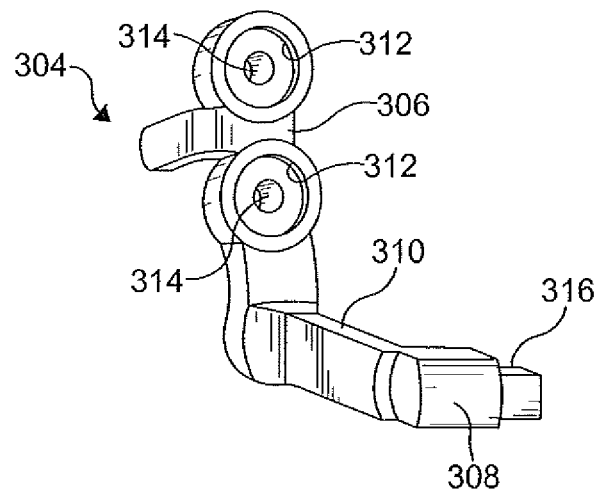
FIG. 22  FIG. 23
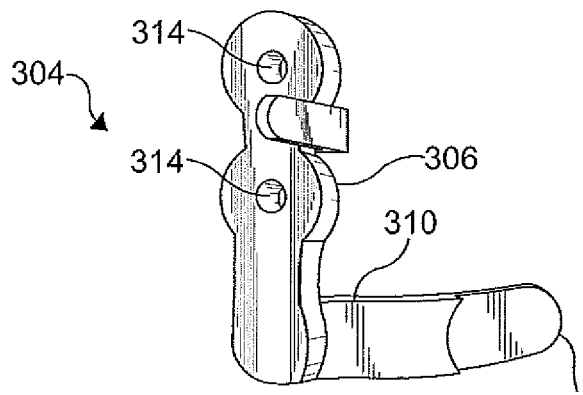
FIG. 24
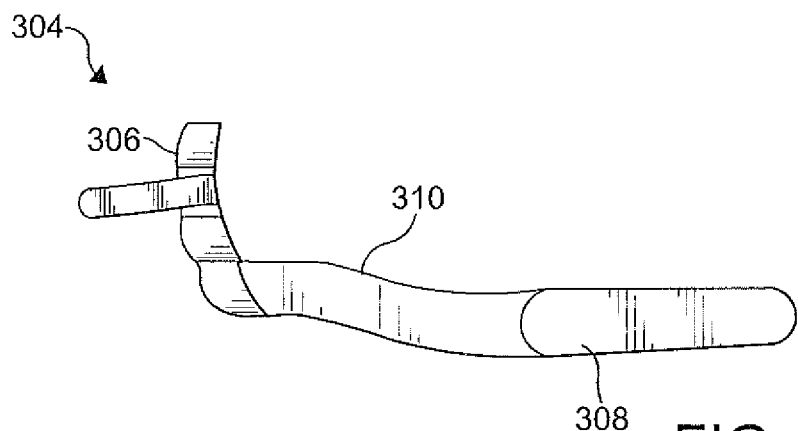
FIG. 25

METHOD AND INTERNAL APPARATUS FOR DETERMINING FINAL POSITION OF DENTATE SKELETON IN ORTHOGNATHIC SURGERY

FIELD OF THE INVENTION

The present invention relates generally to orthognathic, reconstructive jaw, craniofacial or maxillofacial surgery. In particular, the invention is directed to a system and method for positioning a skeletal structure of a patient during orthognathic surgery.

BACKGROUND OF THE INVENTION

Traditional operative orthognathic surgery involves cutting (osteotomizing) a skeletal structure of an upper and/or lower jaw (maxilla and mandible), repositioning the osteotomized dentate skeletal segments with teeth into pre-operatively determined positions, and then fixing the mobile dentate skeletal jaw segments into the pre-determined position with a combination of wires, plates, and screws (rigid fixation) and inter-maxillary fixation (wiring teeth together).

Once the jaw(s) are cut (osteotomized) the dentate skeletal segments are loose and lose a positional relationship relative to each other and to a remaining stable, uncut, facial skeleton. One challenge of successful orthognathic surgery is determining where to position and fix the osteotomized dentate skeletal segments with respect to the remaining, uncut facial skeleton.

Typically, preoperative planning is utilized to predict required changes to the original position of the teeth and jaws of the patient. Anticipated changes to dentate skeletal segments in orthognathic surgery can be determined through various documented methodologies including clinical evaluation of the patient's face and head, cephalometric x-rays, photographs, and through dental models mounted on a dental articulator. More accurately, pre-surgical planning in a digital environment can be performed using computed tomography (e.g. CT/CBCT) and a laser dental (occlusal) scan. Regardless of the methodology utilized in a pre-operative planning, there is currently no accurate technique for translating planned skeletal movements to intra-operative stable skeletal reference points or landmarks.

Intra-operative surgical occlusal splints are important traditional devices for determining the relationship of the teeth of the upper and lower jaws during orthognathic surgery. The occlusal surgical splints can be manufactured from computed tomography and digital dental models or from traditional plaster dental models. Regardless of how dental occlusal splints are manufactured, the splints secure only changes in dental relationships, thereby providing no reference for final intra-operative repositioning of the dentate skeletal segments relative to the uncut facial skeleton. While splints assist in determining changes in dental or occlusal relationships, lacking is a method to precisely determine the final skeletal position of the osteotomized dentate skeletal segments in orthognathic surgery.

Specifically, when a dentate skeletal segment of the face is cut or osteotomized, the loose mobile skeletal segment must be related back to a stable (uncut) facial skeleton assuming a final post-osteotomy position. For example, in the most common orthognathic procedure performed, LeFort I maxillary osteotomy, (horizontal cut across the maxilla at the approximate level of the nasal floor) following completion of the upper jaw transverse cut or osteotomy, the dentate skeletal segment is loose or mobile.

Traditionally, the mobile maxillary (LeFort I) dentate skeleton segment is related to the uncut lower jaw or mandible for its required stable relationship by wiring the maxillary dentition or teeth to the dentition or teeth of the mandible through a dental occlusal splint, and then rotating the entire maxillary/mandibular complex upward until it abuts with the stable facial skeleton above. Unfortunately, the mandible itself is inherently unstable due to its rotational and translational relationship to two highly mobile joints (temporomandibular joints or TMJs). Stability of the mandible is attempted by manually placing the mandibular condyles (joint heads of the mandible) into a specific location within the joint space of the skull base (TMJ fossa).

The relation of the mandible when the mandibular condyles are in the most posterior superior unrestrained positions in the temporal bone glenoid fossa is known as Centric Relation (CR). With the mandible in CR (held manually typically by an assistant), the mandible is rotated with the attached maxillary segment to relate the osteotomized maxilla or loose dentate skeleton to the remaining facial skeleton using an "estimated" centric relation. The complex of bone and teeth are manually held in this position while the maxillary skeletal segment is fixated (wires/plates/screws) to the uncut facial skeleton. The entire process can be wrought with errors and problems.

In an anesthetized supine (lying on one's back) patient, the TMJ joints are lax and precise joint position is difficult to determine. Asymmetric positioning of the mandible can easily occur with only one of the TMJs in CR. Many patients undergoing orthognathic surgery have abnormal or dysplastic or absent TMJs making centric relation determinations difficult or impossible. Because CR relationships are determined manually (by feel only; the joint spaces are not visualized directly) the technique is very susceptible to error. This susceptibility is exacerbated by the fact that the CR position needs to be manually maintained for an extended time period intra-operatively while applying fixation to the maxilla in its new position. Shifting of the hand while holding the mandible, even slightly, can dramatically alter CR positioning. In addition, CR positioning of the mandible/maxillary complex also has no determination in the final vertical positioning of the maxilla. Final vertical placement of the osteotomized dentate skeletal segment of the maxilla is done in an entirely subjective fashion based on the surgeon's clinical determination in an anesthetized, supine, and facially swollen patient.

When a two jaw surgery (upper and lower, bimaxillary, double jaw) is performed, the maxilla is initially repositioned through the method described above. Next, the lower jaw or mandible is cut and repositioned based on the new maxillary position. This procedure is complicated by all of the problems related above with single jaw surgery, then compounded with the addition of the second jaw.

As an example, U.S. Pat. No. 6,726,479 and U.S. Pub. Appl. No. 2004/0166469 to Tremont disclose a technique utilizing a modified RED I device (KLS Martin, L.P., Jacksonville, Fla.) intra-operatively in order to determine skeletal relationships. Through a series of out rigging devices, an external bite is registered on a halo and compared to planned surgical changes. The halo is an externally mounted neurosurgical halo device which is very bulky and risks brain perforation with penetrating scalp pins. The registration bite with the RED I device can slip or torque easily, completely eliminating all accuracy. The halo itself is not completely rigid and can slip or torque easily, completely eliminating all accuracy. The device is expensive and impractical for intra-operative use in traditional orthognathic surgery.

U.S. Pat. No. 4,639,220 to Nara discloses a complicated technique utilizing a bulky, external halo frame similar to that of the Tremont patent (U.S. Pat. No. 6,726,479). The device described by Nara is complicated and is deficient for at least the same reasons as Tremont, discussed herein above.

As a further example, an article by Perkins et al., (Perkins, S., et. al.: "A Modified Boley Gauge for Accurate Measurement During Maxillary Osteotomies". J Oral Maxillofac Surg 50:1018-1019, 1992) discloses a modified Boley gauge (Walter Lorenz) where a caliper is attached to a K-wire drilled into the skull of the patient intra-operatively. Changes in jaw position during surgery are measured, indicating change from original positions. The method described in the article by Perkins et al. is deficient because it only measures changes in dental positions. Furthermore, a minimal movement or torque of the long external wire required by the method of Perkins et al., completely eliminates accuracy of all measurements involved.

It would be desirable to have a simplified apparatus, system, and method for positioning a skeletal structure during orthognathic surgery, wherein disadvantages of the prior art are overcome by eliminating a dependency on Centric Relation (CR) for dentate skeletal repositioning.

SUMMARY OF THE INVENTION

Concordant and consistent with the present invention, an apparatus, system, and method for positioning a skeletal structure during orthognathic surgery, wherein disadvantages of the prior art are overcome by eliminating a dependency on Centric Relation (CR) for dentate skeletal repositioning, has been discovered.

In one embodiment, a skeletal positioning apparatus comprises: a splint having a main body coupled to a skeletal structure of a patient; and a positioning guide having a skeletal footplate, a splint footplate, and an arm coupling the skeletal footplate and the splint footplate, the skeletal footplate including an aperture formed therein and the splint footplate including a means for releasably coupling the positioning guide to the splint, wherein a relative position and orientation of the skeletal footplate and the splint footplate is pre-determined to align a portion of the skeletal footplate with a pre-defined portion of the skeletal structure of the patient.

The invention also provides methods for positioning a skeletal structure of a patient.

One method comprises the steps of: coupling a splint to a portion of the skeletal structure of the patient; coupling a pre-osteotomy positioning guide to the splint; designating a skeletal reference point based upon a position of the pre-osteotomy positioning guide relative to the skeletal structure; decoupling the pre-osteotomy positioning guide from the splint; performing a surgical operation on the skeletal structure of the patient; coupling a post-osteotomy positioning guide to the splint; and aligning a portion of the post-osteotomy positioning guide with the skeletal reference point to position the skeletal structure of the patient in a pre-determined post-osteotomy position.

Another method comprises the steps of: generating a pre-osteotomy model of the skeletal structure of the patient; generating a post-osteotomy model of the skeletal structure of the patient; forming a splint based upon at least one of the pre-osteotomy model and the post-osteotomy model; forming a pre-osteotomy positioning guide based on the pre-osteotomy model of the skeletal structure; forming a post-osteotomy positioning guide based on the post-osteotomy model of the skeletal structure; coupling the splint to a portion of the skeletal structure of the patient; coupling the pre-osteotomy positioning guide to the splint; designating a skeletal reference point based upon a position of the pre-osteotomy positioning guide relative to the skeletal structure; decoupling the pre-osteotomy positioning guide from the splint; performing a surgical operation on the skeletal structure of the patient; coupling the post-osteotomy positioning guide to the splint; and aligning a portion of the post-osteotomy positioning guide with the skeletal reference point to position the skeletal structure of the patient in a pre-determined post-osteotomy position.

BRIEF DESCRIPTION OF THE DRAWINGS

The above, as well as other advantages of the present invention, will become readily apparent to those skilled in the art from the following detailed description of the preferred embodiment when considered in the light of the accompanying drawings in which:

FIG. 16 is a bottom plan view of an occlusal splint of the surgical positioning apparatus and system of FIG. 14;

FIG. 17 is a bottom perspective view of a pre-osteotomy positioning guide of the surgical positioning apparatus and system of FIG. 14;

FIG. 18 is a front perspective view of the pre-osteotomy positioning guide of FIG. 17;

FIG. 19 is a side elevational view of the pre-osteotomy positioning guide of FIG. 17;

FIG. 22 is a bottom perspective view of a post-osteotomy positioning guide of the surgical positioning apparatus and system of FIG. 20;

FIG. 23 is a front perspective view of the post-osteotomy positioning guide of FIG. 22;

FIG. 24 is a rear perspective view of the post-osteotomy positioning guide of FIG. 22;

FIG. 25 is a side elevational view of the post-osteotomy positioning guide of FIG. 22.

DETAILED DESCRIPTION OF EXEMPLARY EMBODIMENTS OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Figure 1:
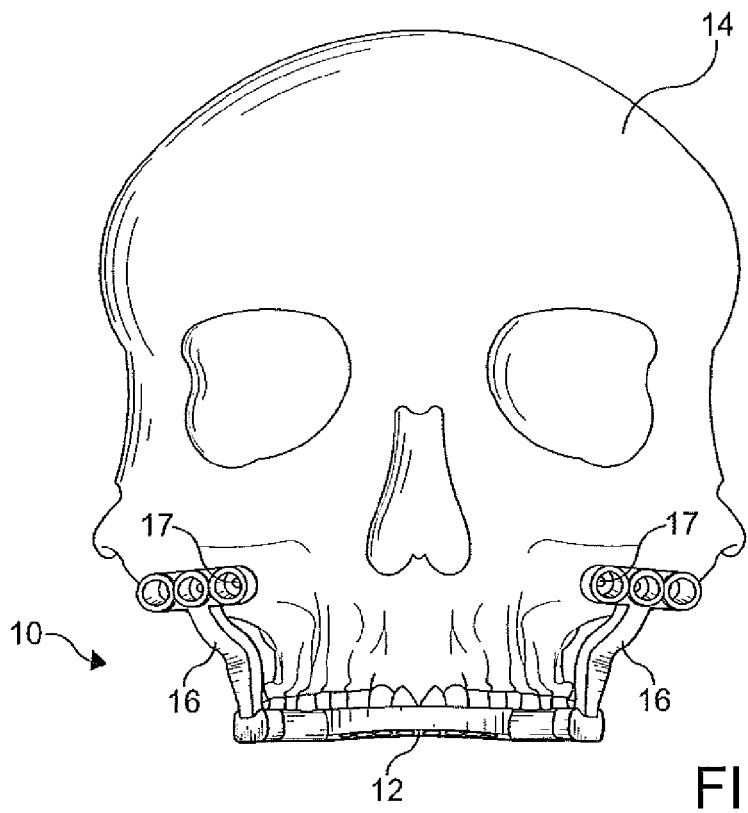
FIG. 1 is a front elevational view of a surgical positioning apparatus and system coupled to a skeletal structure according to an embodiment of the present invention.
Figure 2:
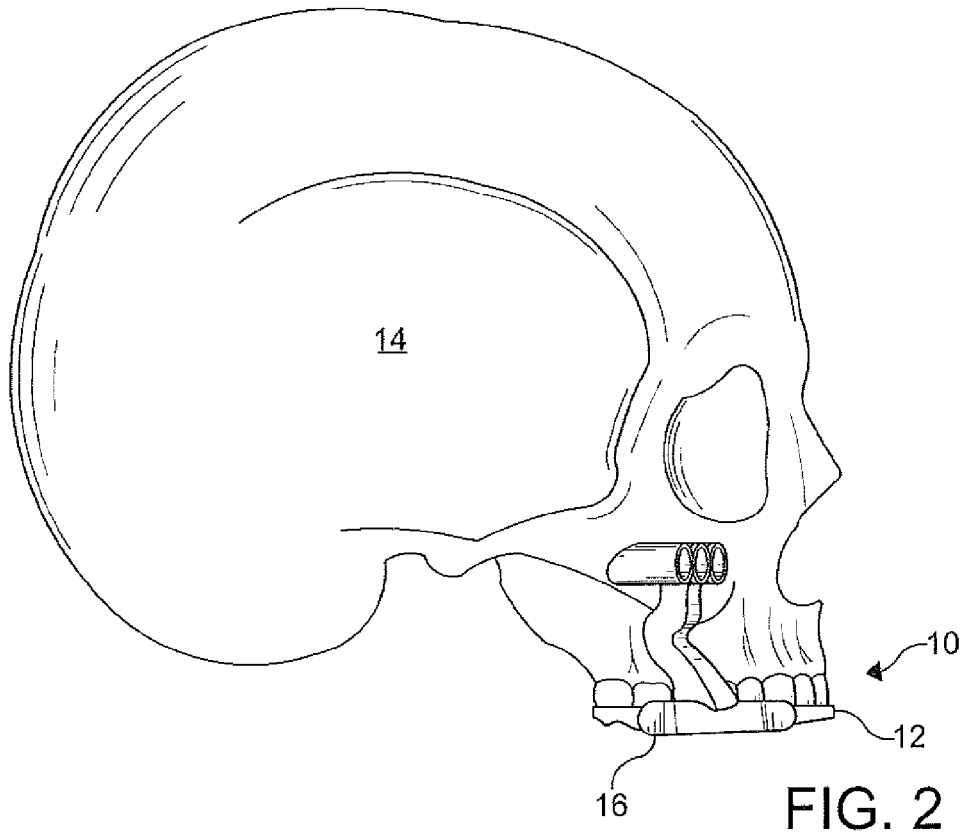
FIG. 2 is a side elevational view of the surgical positioning apparatus and system of FIG. 1.
Figure 3:
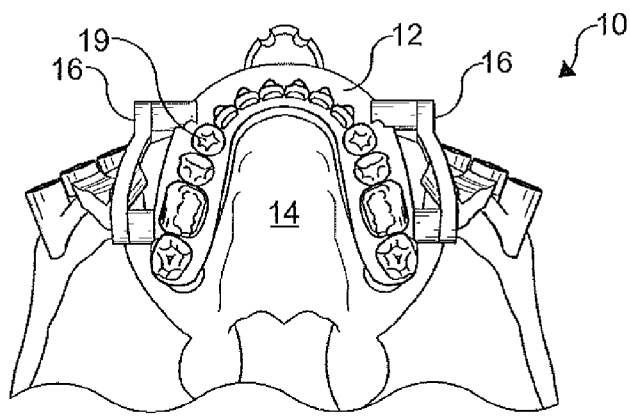
FIG. 3 is a bottom plan view of the surgical positioning apparatus and system of FIG. 1.

FIGS. 1-3 illustrate a surgical positioning apparatus and system 10 for providing three dimensional (3-D) positioning and fixation of the jaws (maxilla and mandible) and teeth (dentate skeleton) of a patient during orthognathic (maxillo-facial) surgery. As shown, the system 10 is in an initial (pre-osteotomy or prior to a cutting procedure) configuration and includes an occlusal splint 12 coupled to a skeletal structure 14 of the patient and a pair of initial or pre-osteotomy positioning guides 16 releasably coupled to the splint 12 for marking or designating a plurality of skeletal reference points 17. The term osteotomy is used as an illustrative example. However, it is understood that the system 10 can be used in other operations and procedures.

Figure 4:
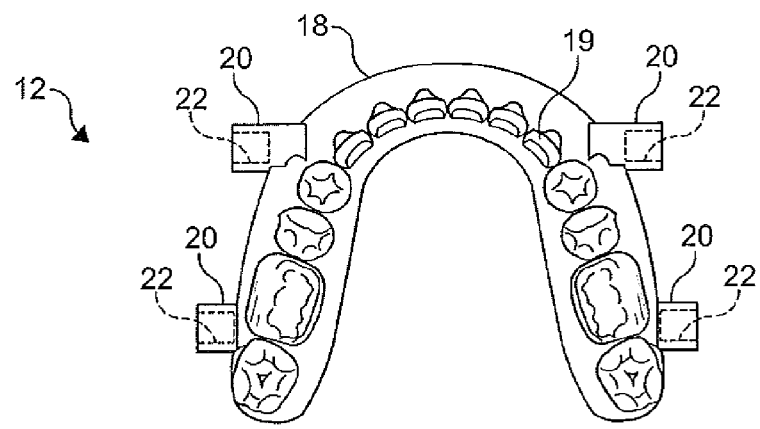
FIG. 4 is a bottom plan view of an occlusal splint of the surgical positioning apparatus and system of FIG. 1.
Figure 5:
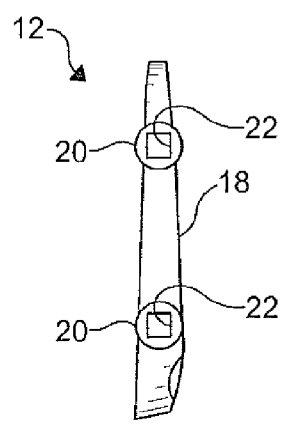
FIG. 5 is a side elevational view of the occlusal splint of FIG. 4.

As more clearly shown in FIGS. 4-5, the occusal splint 12 includes a main body 18 molded to include a plurality of dental markings 19 to fit an upper arch of the teeth of the patient. It is understood that the splint 12 can be molded for the lower arch of teeth. The main body 18 includes a pair of spaced apart connectors 20 disposed on an anterior and a posterior portion of the splint 12, bilaterally. Each of the connectors 20 extends from the main body 18 and includes a rounded exterior contour. A hollow cut-out or cavity 22 is formed in each of the connectors 20. As a non-limiting, the cavity 22 of each of the connectors 20 has a generally square cross-section for precise fitting of an associated retaining insert. However, the connectors 20 and cavities 22 can have any size, shape, and contour. In certain embodiments, the connectors 20 are manufactured to be easily removed from the main body 18 to minimize intraoral irritation to the patient after the surgical operation is complete.

Figure 6:
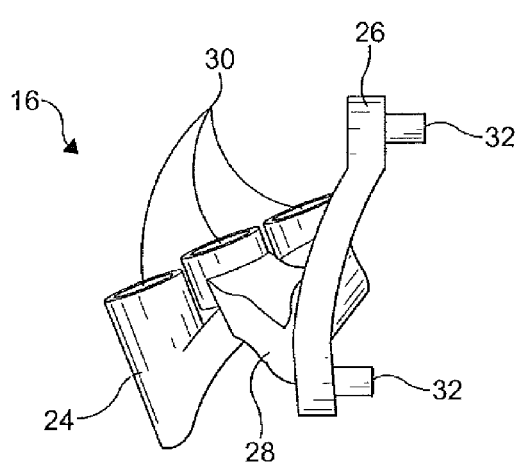
FIG. 6 is a bottom plan view of a pre-osteotomy positioning guide of the surgical positioning apparatus and system of FIG. 1.
Figure 7:
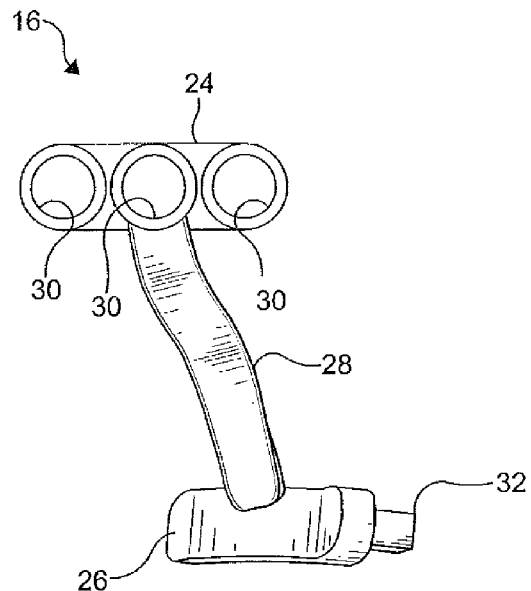
FIG. 7 is a front elevational view of the pre-osteotomy positioning guide of FIG. 6.
Figure 8:
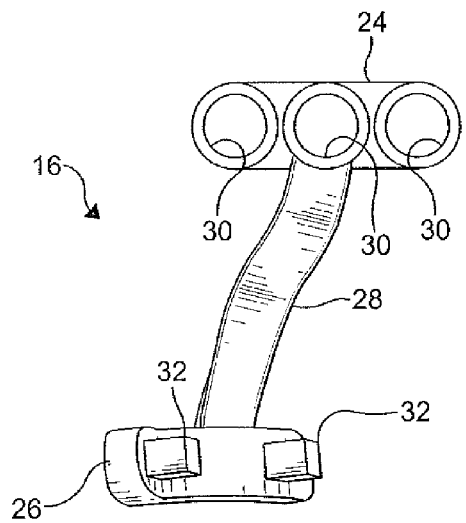
FIG. 8 is a rear elevational view of the pre-osteotomy positioning guide of FIG. 6.

As more clearly shown in FIGS. 6-8, each of the pre-osteotomy positioning guides 16 includes a skeletal footplate 24, a splint footplate 26, and an arm 28 coupling the skeletal footplate 24 to the splint footplate 26.

The skeletal footplate 24 is designed to substantially follow a contour of the maxillary/malar skeleton. However, it is understood that the skeletal footplate 24 can have any shape and size based on the specific needs of the surgical scenario. The skeletal footplate 24 contains round perforations 30 or apertures used as locators and guides to mark or designate the skeletal reference points 17. As a non-limiting example, the skeletal reference points 17 are surgically created by drilling into the skeletal structure 14 using the perforations 30 as an exact guide. It is understood that the drilling can be assisted by the use of commercially available "surgical guides".

The splint footplate 26 includes a plurality of retaining inserts 32 or male connectors for insertion into the cavity 22 formed in each of the connectors 20 attached to the occlusal splint 12. As a non-limited example the retaining inserts 32 have a generally square cross-section to substantially match the shape of an associated one of the cavities 22. It is understood that the retaining inserts 32 can have any size and shape. It is further understood that other means for selectively and releasably coupling the splint footplate 26 to the splint 12 can be used. As a non-limiting example, the splint footplate 26 can include a plurality of cavities (not shown) and the splint 12 can include a plurality of associated retaining inserts or extensions (not shown).

The arm 28 is coupled to the skeletal footplate 24 and the splint footplate 26 to provide a pre-defined relative positioning therebetween. As a non-limiting example a relative position and orientation of the skeletal footplate 24 and the splint footplate 26 is pre-determined to align a portion of the skeletal footplate 24 with a pre-defined portion (e.g. skeletal landmarks) of the skeletal structure 14 of the patient. As a further non-limiting example, the arm 28 is designed to closely fit the anatomical contours of a facial skeleton of the patient. It is understood that the arm 28 can have any size and shape.

Figure 9:
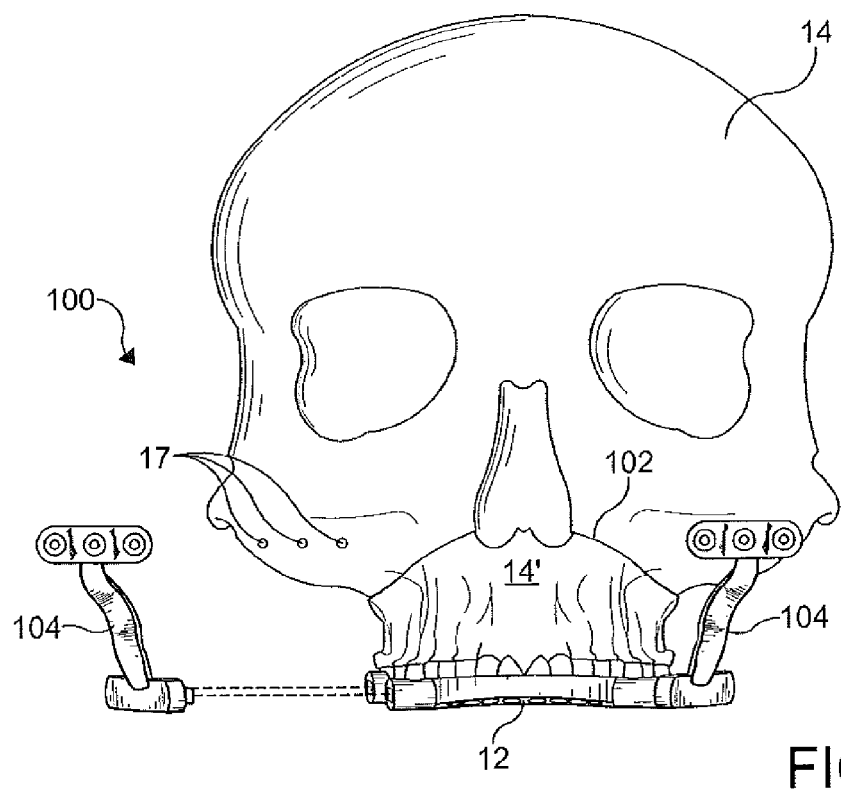
FIG. 9 is a partially exploded front elevational view of a surgical positioning apparatus and system coupled to a skeletal structure according to another embodiment of the present invention.
Figure 10:
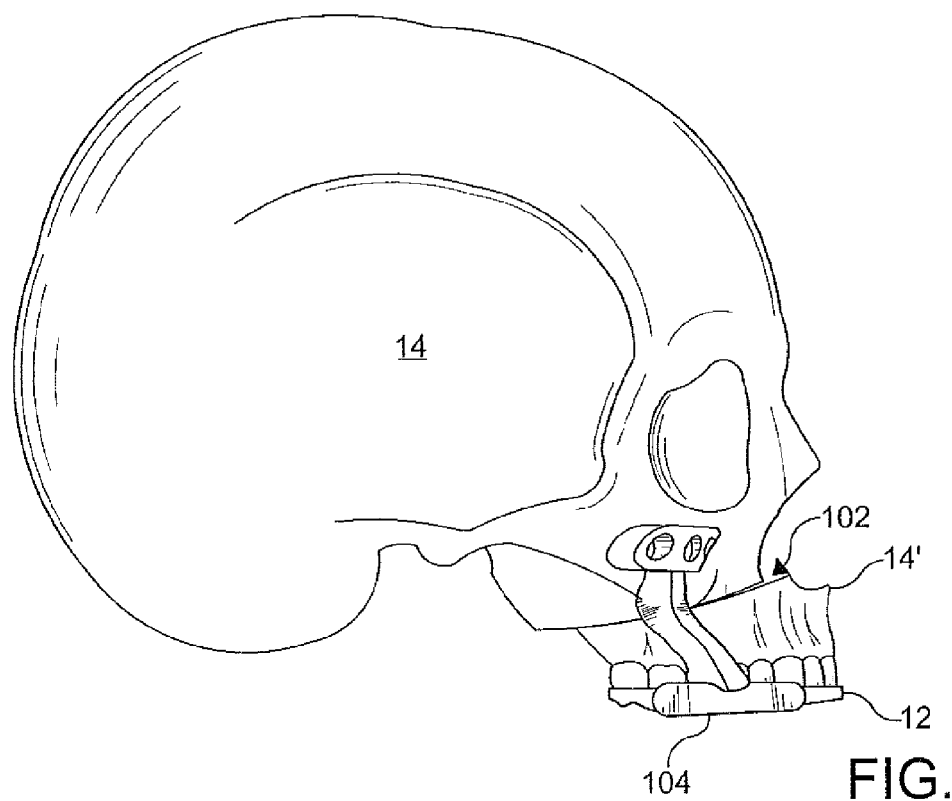
FIG. 10 is a side elevational view of the surgical positioning apparatus and system of FIG. 9.

FIGS. 9-10 illustrate a surgical positioning apparatus and system 100 according to another embodiment, wherein the surgical positioning system 100 is similar to the system 10 except as described herein below. As shown, the system 100 is in a final (post-osteotomy or after a cutting/sectioning procedure) configuration and includes the occlusal splint 12 coupled to an osteotomized skeletal segment 14' (e.g. below a LeFort I cut line 102) of the skeletal structure 14 of the patient and a pair of final or post-osteotomy positioning guides 104 releasably coupled to the splint 12. The term osteotomy is used as an illustrative example. However, it is understood that the system 100 can be used in other operations and procedures.

Figure 11:
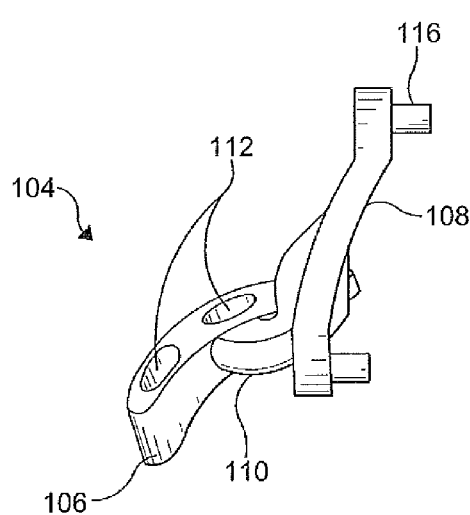
FIG. 11 is a bottom plan view of a post-osteotomy positioning guide of the surgical positioning apparatus and system of FIG. 9.
Figure 12:
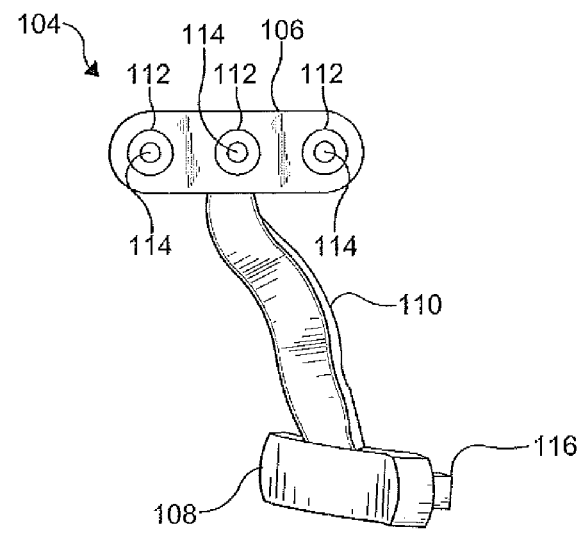
FIG. 12 is a front elevational view of the post-osteotomy positioning guide of FIG. 9.
Figure 13:
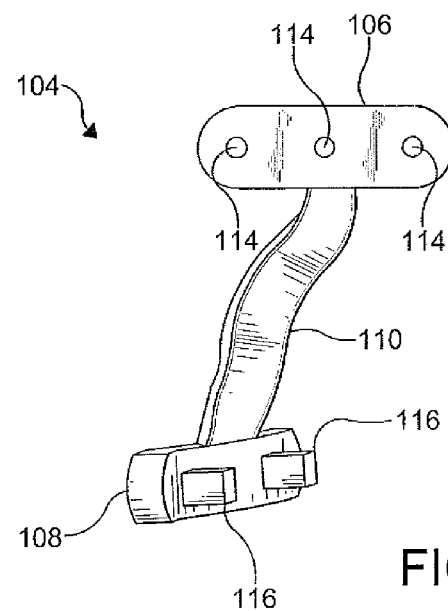
FIG. 13 is a rear elevational view of the post-osteotomy positioning guide of FIG. 9.

As more clearly shown in FIGS. 11-13, each of the post-osteotomy positioning guides 104 includes a skeletal footplate 106, a splint footplate 108, and an arm 110 coupling the skeletal footplate 106 to the splint footplate 108.

The skeletal footplate 106 is designed to substantially follow a contour of the maxillary/malar skeleton. However, it is understood that the skeletal footplate 106 can have any shape and size based on the specific needs of the surgical scenario. The skeletal footplate 106 includes a plurality of recessed regions 112 with a through-hole or aperture 114 formed therein. It is understood that the apertures 114 are used as locators to align the skeletal footplate 106 with the skeletal reference points 17.

The splint footplate 108 includes a plurality of retaining inserts 116 or male connectors for insertion into the cavities 22 formed in the connectors 20 attached to the occlusal splint 12. As a non-limited example the retaining inserts 116 have a generally square cross-section to substantially match the shape of the cavities 22. It is understood that the retaining inserts 116 can have any size and shape. It is further understood that other means for selectively and releasably coupling the splint footplate 108 to the splint 12 can be used. As a non-limiting example, the splint footplate 108 can include a plurality of cavities (not shown) and the splint 12 can include a plurality of associated retaining inserts or extensions (not shown).

The arm 110 is coupled to the skeletal footplate 106 and the splint footplate 108 to provide a pre-defined relative positioning therebetween. As a non-limiting example a relative position and orientation of the skeletal footplate 106 and the splint footplate 108 is pre-determined to align a portion of the skeletal footplate 106 with the skeletal reference points 17. As a further non-limiting example, the arm 110 is designed to closely fit the anatomical contours of a facial skeleton of the patient. It is understood that the arm 110 can have any size and shape.

Figure 14:
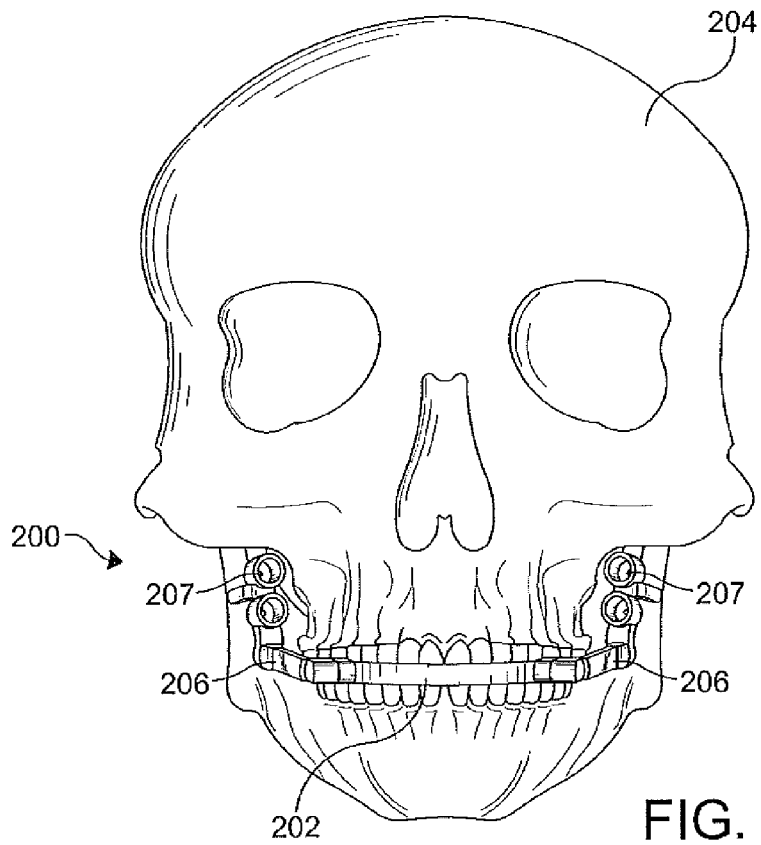
FIG. 14 is a front elevational view of a surgical positioning apparatus and system coupled to a skeletal structure according to another embodiment of the present invention.
Figure 15:
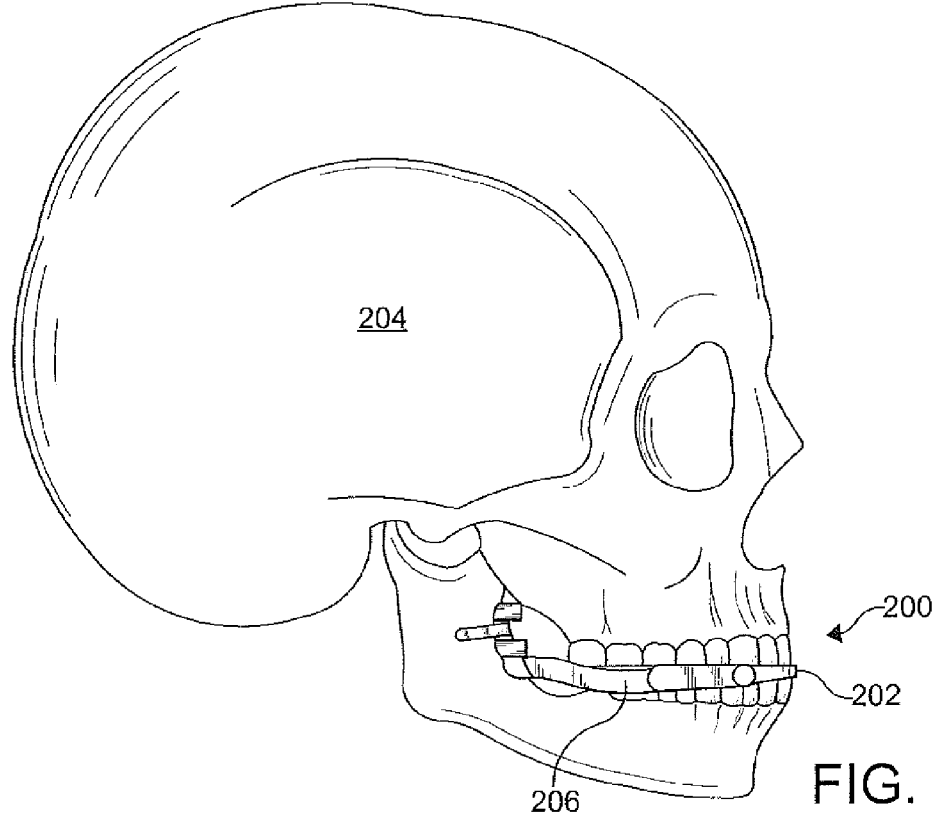
FIG. 15 is a side elevational view of the surgical positioning apparatus and system of FIG. 14.

FIGS. 14-15 illustrate a surgical positioning apparatus and system 200 according to another embodiment of the present invention similar to the system 10, except as described below. As shown, the system 200 is in an initial (pre-osteotomy) configuration and includes an occlusal splint 202 coupled to a skeletal structure 204 of the patient and a pair of initial or pre-osteotomy positioning guides 206 releasably coupled to the splint 202 for marking or designating a plurality of skeletal reference points 207. The term osteotomy is used as an illustrative example. However, it is understood that the system 200 can be used in other operations and procedures.

As more clearly shown in FIG. 16, the occlusal splint 202 includes a main body 208 molded to include a plurality of dental markings 209 to fit both an upper arch and lower arch of the teeth of the patient. The main body 208 includes a pair of spaced apart connectors 210 disposed on an anterior and a posterior portion of the splint 202, generally bilaterally. Each of the connectors 210 extends from the main body 208 and includes a rounded exterior contour. A hollow cut-out or cavity 212 is formed in each of the connectors 210. As a non-limiting, the cavity 212 of each of the connectors 210 has a generally square cross-section for precise fitting of an associated retaining insert. However, the connectors 210 and cavities 212 can have any size, shape, and contour. In certain embodiments, the connectors 210 are manufactured to be easily removed from the main body 208 to minimize intraoral irritation to the patient after the surgical operation is complete.

As more clearly shown in FIGS. 17-19, each of the pre-osteotomy positioning guides 206 includes a skeletal footplate 214, a splint footplate 216, and an arm 218 coupling the skeletal footplate 214 to the splint footplate 216.

The skeletal footplate 214 is designed to substantially follow a contour of the mandible skeleton. However, it is understood that the skeletal footplate 214 can have any shape and size based on the specific needs of the surgical scenario. The skeletal footplate 214 contains round perforations 220 or apertures used as locators and guides to mark or designate the skeletal reference points 207. As a non-limiting example, the skeletal reference points 207 are surgically created by drilling into the skeletal structure 204 using the perforations 220 as an exact guide. It is understood that the drilling can be assisted by the use of commercially available "surgical guides".

The splint footplate 216 includes a plurality of retaining inserts 222 or male connectors for insertion into the cavity 212 formed in each of the connectors 210 attached to the occlusal splint 202. As a non-limited example the retaining inserts 222 have a generally square cross-section to substantially match the shape of an associated one of the cavities 212. It is understood that the retaining inserts 222 can have any size and shape. It is further understood that other means for selectively and releasably coupling the splint footplate 216 to the splint 202 can be used. As a non-limiting example, the splint footplate 216 can include a plurality of cavities (not shown) and the splint 202 can include a plurality of associated retaining inserts or extensions (not shown).

The arm 218 is coupled to the skeletal footplate 214 and the splint footplate 216 to provide a pre-defined relative positioning therebetween. As a non-limiting example a relative position and orientation of the skeletal footplate 214 and the splint footplate 216 is pre-determined to align a portion of the skeletal footplate 214 with a pre-defined portion (e.g. skeletal landmarks) of the skeletal structure 204 of the patient. As a further non-limiting example, the arm 218 is designed to closely fit the anatomical contours of a facial skeleton of the patient. It is understood that the arm 218 can have any size and shape.

Figure 20:
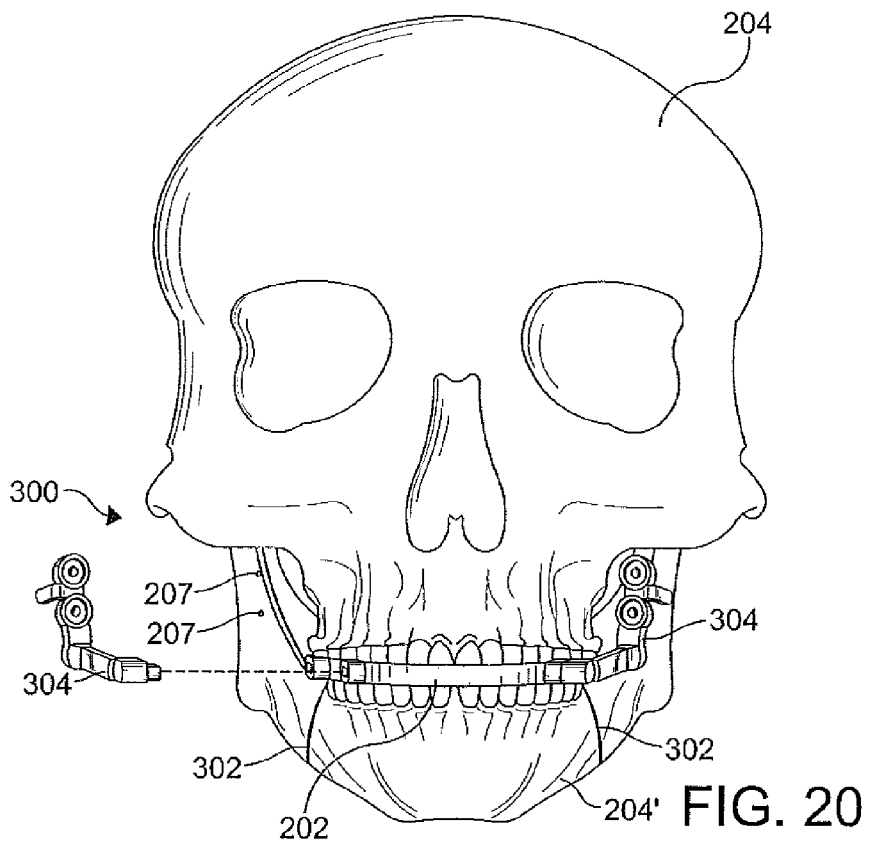
FIG. 20 is a partially exploded front elevational view of a surgical positioning apparatus and system coupled to a skeletal structure according to another embodiment of the present invention.
Figure 21:
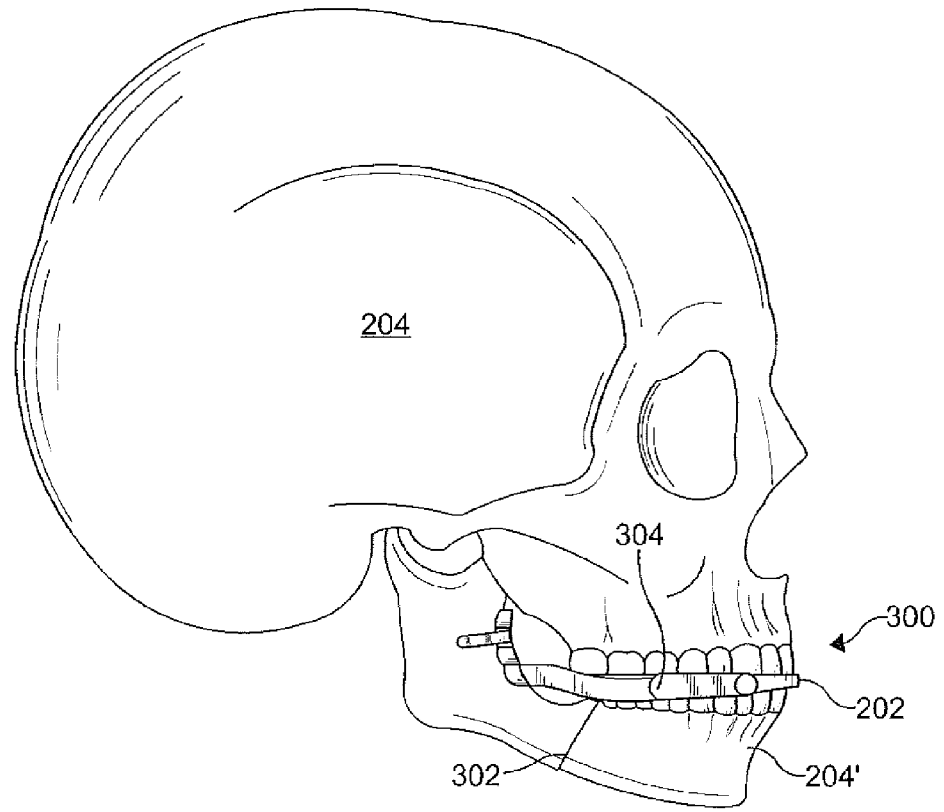
FIG. 21 is a side elevational view of the surgical positioning apparatus and system of FIG. 20.

FIGS. 20-21 illustrate a surgical positioning apparatus and system 300 according to another embodiment, wherein the surgical positioning system 300 is similar to the system 200 except as described herein below. As shown, the system 300 is in a final (post-osteotomy) configuration and includes the occlusal splint 202 coupled to an osteotomized skeletal segment 204' (e.g. between a pair of cut lines 302) of the skeletal structure 204 of the patient and a pair of final or post-osteotomy positioning guides 304 releasably coupled to the splint 202. The term osteotomy is used as an illustrative example. However, it is understood that the system 300 can be used in other operations and procedures.

As more clearly shown in FIGS. 22-25, each of the post-osteotomy positioning guides 304 includes a skeletal footplate 306, a splint footplate 308, and an arm 310 coupling the skeletal footplate 306 to the splint footplate 308.

The skeletal footplate 306 is designed to substantially follow a contour of the mandible skeleton. However, it is understood that the skeletal footplate 306 can have any shape and size based on the specific needs of the surgical scenario. The skeletal footplate 306 includes a plurality of recessed regions 312 with a through-hole or aperture 314 formed therein. It is understood that the apertures 314 are used as locators to align the skeletal footplate 306 with the skeletal reference points 207.

The splint footplate 308 includes a plurality of retaining inserts 316 or male connectors for insertion into the cavities 212 formed in the connectors 210 attached to the occlusal splint 202. As a non-limited example the retaining inserts 316 have a generally square cross-section to substantially match the shape of the cavities 212. It is understood that the retaining inserts 316 can have any size and shape. It is further understood that other means for selectively and releasably coupling the splint footplate 308 to the splint 202 can be used. As a non-limiting example, the splint footplate 308 can include a plurality of cavities (not shown) and the splint 202 can include a plurality of associated retaining inserts or extensions (not shown).

The arm 310 is coupled to the skeletal footplate 306 and the splint footplate 308 to provide a pre-defined relative positioning therebetween. As a non-limiting example a relative position and orientation of the skeletal footplate 306 and the splint footplate 308 is pre-determined to align a portion of the skeletal footplate 306 with the skeletal reference points 207. As a further non-limiting example, the arm 310 is designed to closely fit the anatomical contours of a facial skeleton of the patient. It is understood that the arm 310 can have any size and shape.

Figure 26:
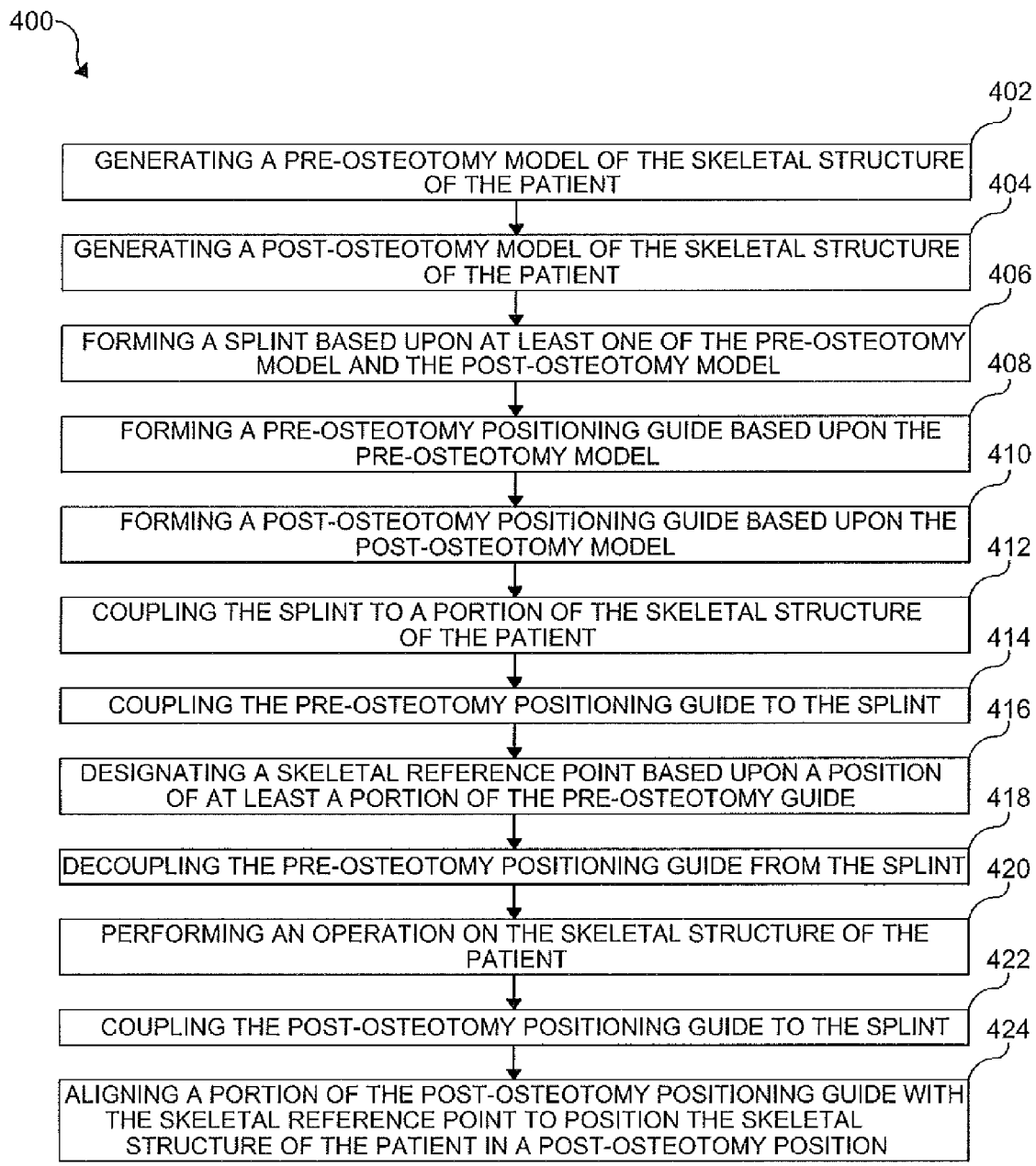
FIG. 26 is a schematic flow diagram of a method form positioning a skeletal structure of a patient according to an embodiment of the present invention.

FIG. 26 illustrates a method 400 for positioning the osteotomized skeletal segment 14', 204' of the skeletal structure 14, 204 of the patient during an orthognathic operation according to an embodiment of the present invention.

Initially, a skeletal data is obtained from a computerized tomography (CT) scan or a cone beam computerized tomography (CBCT) scan (referred to herein as scans). The data is relied upon to generate a pre-osteotomy model of the skeletal structure 14, 204 of the patient and a post-osteotomy model of the skeletal structure 14, 204 of the patient, as shown in steps 402 and 404. As a non-limiting example, the pre-osteotomy model includes stable and identifiable skeletal landmarks that can be designated by the skeletal reference points 17, 207. In certain embodiments, the skeletal reference points 17, 207 are pre-defined by a computer based upon skeletal landmarks in the pre-osteotomy model. As a further non-limiting example, the pre-osteotomy model can be manually manipulated or automatically manipulated based upon a surgical plan to generate the post-osteotomy model and the post-osteotomy position of the skeletal structure 14, 204.

As shown in step 406, the occlusal splint 12, 202 is formed based upon at least one of the pre-osteotomy model and the post operation model. As a non-limiting example, the splint 12, 202 can be fabricated using stereolitography technology. It is understood that the splint 12, 202 can be customized for any patient.

As shown in step 408, the pre-osteotomy positioning guides 16, 206 are generated based on the features and contours of the pre-osteotomy model. As a non-limiting example, the pre-osteotomy positioning guides 16, 206 are fabricated using stereolitography technology. As a further non-limiting example, the pre-osteotomy positioning guides 16, 206 are formed from a photo cured plastic. As another example, the pre-osteotomy positioning guides 16, 206 are designed based on a digital model of at least one of a pre-osteotomy (uncut) maxilla and mandible.

As shown in step 410, the post-osteotomy positioning guides 104, 304 are generated based on the features and contours of the post-osteotomy model. As a non-limiting example, the post-osteotomy positioning guides 104, 304 are fabricated using stereolitography technology. As a further non-limiting example, the post-osteotomy positioning guides 104, 304 are from a photo cured plastic. As another example, the post-osteotomy positioning guides 104, 304 are designed based on a digital model of at least one of a post-osteotomy (cut) maxilla and mandible.

At surgery, after exposure of the facial skeleton, the occlusal splint 12, 202 is coupled (e.g. wired) to a portion of the skeletal structure 14, 204 (e.g. an upper arch of teeth), as shown in step 412. The pre-osteotomy positioning guides 16, 206 are coupled to the splint 12, 202 on opposite sides thereof, as shown in step 414. Using the apertures 30, 220 as a guide, the skeletal reference points 17, 207 are designated (e.g. marked, drilled, burred, or the like) as shown in step 416. As a non-limiting example, the skeletal reference points 17 are disposed superior to the LeFort I osteotomy line 102 on both sides of the facial skeleton. As a further non-limiting example, the skeletal reference points 17, 207 demarcate pre-defined skeletal landmarks of the skeletal structure 14, 204 of the patient. In certain embodiments, a tool, sleeve, or drill guide (plastic or metal) is placed into the apertures 30, 220 of the skeletal footplate 24, 214 to assist in the exact designation/marking.

In step 418, the pre-osteotomy positioning guides 16, 206 are decoupled from the occlusal splint 12, 202. In step 420, a surgical operation is performed on the skeletal structure 14, 204. As a non-limiting example, a skeletal osteotomy or bone cut is performed accordingly to a pre-surgical plan.

In step 422, the splint footplate 108, 308 of the post-osteotomy positioning guide 104, 304 is coupled to the splint 12, 202. As a non-limiting example, the post-osteotomy positioning guide 104, 304 is held in position by inserting a "positioning jig" (not shown) through the apertures 114, 314 and into the previously drilled skeletal reference points 17, 207. With the apertures 114, 314 of the skeletal footplate 106, 306 aligned with the skeletal reference points 17, 207, the osteotomized skeletal segment 14', 204' is accurately positioned in a post-osteotomy position relative to a stable portion of the skeletal structure 14, 204, as shown in step 424. The osteotomized skeletal segment 14', 204' is secured with known rigid fixation techniques to maintain the post-osteotomy position dictated by the alignment of the post-osteotomy positioning guide 104, 304.

It is understood that intermaxillary wire fixation (IMF) is unnecessary and a final maxillary three-dimensional skeletal positioning and fixation is performed independent of the mandible and determination of CR.

It is further understood that the systems 10, 100, 200, 300 and the method 400 of the present invention can be applied to orthognathic surgery of a lower jaw or mandible. Positioning of a proximal segment of the mandible is also determined through skeletal reference points drilled into the skeletal structure 14, 204 of the patient before osteotomizing the bone at the anterior (ramus) border of the mandible. After the mandible is osteotomized, the distal (dentate) segment of the mandible is repositioned, while preserving the pre-surgical natural CR of the mandibular condyles. In a case in which only the mandible is moved, there is only the need for one mandibular "guide".

The systems 10, 100, 200, 300 and the method 400 of the present invention eliminate the need for external reference points, pins, wires, bulky and expensive head gear and calipers, for positioning teeth and jaws in orthognathic surgery. The systems 10, 100, 200, 300 and method 400 of the present invention simplify orthognathic surgery and minimize a time needed for orthognathic surgery by eliminating the intraoperative need for wiring teeth together. The systems 10, 100, 200, 300 and the method 400 of the present invention minimize error in orthognathic surgery by eliminating the need for knowing (intra-operatively) the CR of the mandible when performing surgery on the upper jaw and teeth. The systems 10, 100, 200, 300 and the method 400 of the present invention allow for single splint surgery, eliminating the need for intermediate and final splints when performing double jaw surgery.

The systems 10, 100, 200, 300 and the method 400 of the present invention allow a surgeon to make precise skeletal changes to an original position of a patient's teeth and jaws (dentate skeleton) without external references and independent of centric relation (CR). The systems 10, 100, 200, 300 and the method 400 of the present invention anatomically and accurately solve the problems inherent to the prior art. The invention is reproducible, affordable, and easily applicable in the operative field, greatly reducing operative time.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:
1. A skeletal positioning apparatus comprising:
a splint having an arch-shaped main body for coupling to a skeletal structure of a patient and a connector disposed on the main body; and
a positioning guide having a skeletal footplate, a splint footplate, and an arm coupling the skeletal footplate and the splint footplate, the skeletal footplate including at least one aperture formed therein and the splint footplate including a means for releasably coupling the positioning guide directly to the main body of the splint at the connector, wherein a relative position and orientation of the skeletal footplate is pre-determined relative to the splint footplate to align a portion of the skeletal footplate with a pre-defined portion of the skeletal structure of the patient when the splint footplate is coupled to the splint.

2. The skeletal positioning apparatus according to claim 1, wherein the splint includes dental markings to fit at least one tooth of the patient.

3. The skeletal positioning apparatus according to claim 1, wherein the splint is adapted to be coupled to an arch of teeth of the patient.

4. The skeletal positioning apparatus according to claim 1, wherein the splint includes a cavity and the means for releasably coupling the positioning guide includes a retaining insert received in the cavity for coupling the positioning guide to the splint, or wherein the splint includes a retaining insert and the means for releasably coupling the positioning guide includes a cavity receiving the retaining insert for coupling the positioning guide to the splint.

5. The skeletal positioning apparatus according to claim 1, wherein the positioning guide is a pre-osteotomy positioning guide and the at least one aperture formed in the skeletal footplate is adapted to be aligned with a pre-defined skeletal landmark of the skeletal structure to assist in demarcating the skeletal landmark.

6. The skeletal positioning apparatus according to claim 1, wherein the positioning guide is a post-osteotomy positioning guide and the at least one aperture formed in the skeletal footplate is adapted to be aligned with a pre-defined demarcation of the skeletal structure to align the skeletal structure of the patient in a post-osteotomy position.

7. A skeletal positioning apparatus for performing orthognathic surgery comprising:
a splint having an arch-shaped main body configured for coupling to an arch of teeth of a patient and including a connector disposed on the main body; and
a positioning guide having a skeletal footplate, a splint footplate, and an arm coupling the skeletal footplate and the splint footplate, the skeletal footplate including at least one aperture formed therein as a guide for marking a skeletal reference point on the patient, and the splint footplate including a retaining insert cooperating with the connector to releasably couple the positioning guide directly to the main body of the splint at the splint footplate,
wherein a relative position and orientation of the skeletal footplate is pre-determined relative to the splint footplate to align a portion of the skeletal footplate with a pre-defined portion of the skeletal structure of the patient when the splint footplate is coupled to the splint.

8. The skeletal positioning apparatus according to claim 7 wherein the connector has a cavity formed therein in which the retaining insert is received.

9. The skeletal positioning apparatus according to claim 7 wherein the skeletal footplate is configured to substantially follow a contour of one of a maxillary/malar skeleton of the patient and a mandible skeleton of the patient.

10. The skeletal positioning apparatus according to claim 7 wherein the arm is configured to closely fit anatomical contours of a facial skeleton of the patient.

11. The skeletal positioning apparatus according to claim 7 wherein the positioning guide is a pre-osteotomy positioning guide and the at least one aperture formed in the skeletal footplate is adapted to be aligned with a pre-defined reference skeletal landmark of the skeletal structure to assist in demarcating the reference skeletal landmark.

12. The skeletal positioning apparatus according to claim 7 wherein the positioning guide is a post-osteotomy positioning guide and the at least one aperture formed in the skeletal footplate is adapted to be aligned with a pre-defined demarcation of a reference skeletal landmark of the skeletal structure to align the skeletal structure of the patient in a post-osteotomy position.

13. The skeletal positioning apparatus according to claim 12 wherein the skeletal footplate has a recess region formed therein surrounding the at least one aperture.

14. The skeletal positioning apparatus according to claim 7 wherein the main body of the splint is configured for coupling to fit at least one of upper and lower arches of teeth of the patient.

15. A skeletal positioning apparatus for performing orthognathic surgery comprising:
a splint having an arch-shaped main body configured for coupling to an arch of teeth of a patient and including a plurality of connectors disposed on the main body; and
a pair of positioning guides each having a skeletal footplate, a splint footplate, and an arm coupling the skeletal footplate and the splint footplate, the skeletal footplates each including at least one aperture formed therein as a guide for marking a skeletal reference landmark on the patient, and the splint footplates each including at least one retaining insert cooperating with an associated one of the connectors to releasable couple the positioning guides directly to the main body of the splint at the splint footplates,
wherein a relative position and orientation of each of the skeletal footplates is pre-determined relative to the coupled splint footplate to align a portion of the skeletal footplate with a pre-defined portion of the skeletal structure of the patient when the coupled splint footplate is coupled to the splint.

16. The skeletal positioning apparatus according to claim 15 wherein each of the skeletal footplates is configured to substantially follow a contour of one of a maxillary/malar skeleton of the patient and a mandible skeleton of the patient.

17. The skeletal positioning apparatus according to claim 15 wherein each of the arms is configured to closely fit anatomical contours of a facial skeleton of the patient.

18. The skeletal positioning apparatus according to claim 15 wherein each of the positioning guides is a pre-osteotomy positioning guide and the at least one aperture formed in the skeletal footplate is adapted to be aligned with a pre-defined skeletal landmark of the skeletal structure to assist in demarcating the skeletal reference landmark.

19. The skeletal positioning apparatus according to claim 15 wherein each of the positioning guides is a post-osteotomy positioning guide and the at least one aperture formed in the skeletal footplate is adapted to be aligned with a pre-defined demarcation of the skeletal structure to align the skeletal structure of the patient in a post-osteotomy position.

* * * * *